(12) United States Patent
Chang et al.

(10) Patent No.: US 8,278,353 B2
(45) Date of Patent: *Oct. 2, 2012

(54) ENHANCED BIMATOPROST OPHTHALMIC SOLUTION

(75) Inventors: Chin-Ming Chang, Tustin, CA (US); James N. Chang, Newport Beach, CA (US); Rhett M. Schiffman, Laguna Beach, CA (US); R. Scott Jordan, Trabuco Canyon, CA (US); Joan-En Chang-Lin, Tustin, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/370,574

(22) Filed: Feb. 10, 2012

(65) Prior Publication Data

US 2012/0142783 A1    Jun. 7, 2012

Related U.S. Application Data

(63) Continuation of application No. 12/965,514, filed on Dec. 10, 2010, which is a continuation of application No. 11/083,261, filed on Mar. 16, 2005, now Pat. No. 7,851,504.

(51) Int. Cl.
*A61K 31/19* (2006.01)
*A61K 31/215* (2006.01)

(52) U.S. Cl. .................................. 514/530; 514/573
(58) Field of Classification Search .................. 514/530, 514/573
See application file for complete search history.

(56) References Cited

U.S. PATENT DOCUMENTS

| | | | |
|---|---|---|---|
| 4,055,602 A | 10/1977 | Nelson | |
| 4,100,192 A | 7/1978 | Morozowich | |
| 4,122,282 A | 10/1978 | Nelson | |
| 4,123,441 A | 10/1978 | Johnson | |
| 4,128,577 A | 12/1978 | Nelson | |
| 4,171,331 A | 10/1979 | Biddlecom | |
| 4,183,870 A | 1/1980 | Caton | |
| 4,303,796 A | 12/1981 | Nelson | |
| 4,382,953 A | 5/1983 | Ishii | |
| 4,543,353 A | 9/1985 | Faustini | |
| 4,599,353 A | 7/1986 | Bito | |
| 4,812,457 A | 3/1989 | Narumiya | |
| 4,994,274 A | 2/1991 | Chan | |
| 5,034,413 A | 7/1991 | Chan | |
| 5,281,591 A | 1/1994 | Burke | |
| 5,352,708 A | 10/1994 | Woodward | |
| 5,474,979 A | 12/1995 | Ding | |
| 5,510,383 A | 4/1996 | Bishop | |
| 5,545,665 A | 8/1996 | Burk | |
| 5,587,391 A | 12/1996 | Burk | |
| 5,607,978 A | 3/1997 | Woodward | |
| 5,688,819 A | 11/1997 | Woodward | |
| 6,403,649 B1 | 6/2002 | Woodward | |
| 6,596,765 B2 | 7/2003 | Ueno | |
| 6,646,001 B2 | 11/2003 | Hellberg | |
| 6,743,439 B1 | 6/2004 | Castillo | |
| 6,933,289 B2 | 8/2005 | Lyons | |
| 8,017,655 B2 | 9/2011 | Woodward | |
| 2002/0103255 A1 | 8/2002 | Hellberg | |
| 2004/0029771 A1 | 2/2004 | Rigdon | |
| 2004/0115234 A1 | 6/2004 | Gewirtz | |
| 2005/0004074 A1 | 1/2005 | Lyons | |
| 2005/0276867 A1 | 12/2005 | Lyons | |

FOREIGN PATENT DOCUMENTS

| | | |
|---|---|---|
| CA | 2144967 | 3/1994 |
| CA | 2498233 | 3/2004 |
| DE | 2721534 | 12/1977 |
| EP | 0093380 | 11/1983 |
| EP | 0102230 | 3/1984 |
| EP | 0098141 | 11/1984 |
| EP | 0253094 | 1/1988 |
| EP | 0364417 | 4/1990 |
| EP | 0453127 | 10/1991 |
| FR | 2239458 | 2/1975 |
| FR | 2312240 | 12/1976 |
| FR | 2386523 | 11/1978 |
| FR | 2402644 | 4/1979 |
| JP | S49-069636 | 7/1974 |
| JP | S62-215537 | 9/1987 |
| LU | 68940 | 12/1973 |
| WO | WO 90-02553 | 3/1990 |
| WO | 92-008465 | 5/1992 |
| WO | WO 94-06433 | 3/1994 |
| WO | 2002-007731 | 1/2002 |
| WO | WO 2004-013119 | 2/2004 |

OTHER PUBLICATIONS

Burstein, Neal L. et al., "Electrophysiologic and Morphologic Effects of Ophthalmic Preparations on Rabbit Cornea Epithelium," Invest. Ophthalmol. Visual Sci., vol. 16, No. 10, 899-911, Oct. 1977.

Eisenberg, Dan et al., "Bimatoprost and Travoprost: A Review of Recent Studies of Two New Glaucoma Drugs", Survey of Ophthalmology, vol. 47, sup. 1, SI05-S115, Aug. 2002.

Green, Keith et al., "Prednisolone Phosphate Penetration Into and Through the Cornea," Investigative Ophthalmology, vol. 13, No. 4, 316-319, Apr. 1974.

LUMIGAN® monograph in the 57th PDR (2003).

Mealy, N.E. et al., "Ophthalmic Drugs," Drugs of the Future, 27(5), 509-523, 2002.

Medical Review, Application No. 21-275, Center for Drug Evaluation and Research, 2001.

Pfister, Roswell R. et al., "The Effects of Ophthalmic Drugs, Vehicles, and Preservatives on Corneal Epithelium: a Scanning Electron Microscope Study," Effects of Ophthalmic Drugs, vol. 15, No. 4, 246-259, Apr. 1976.

(Continued)

*Primary Examiner* — Zohreh Fay

(74) *Attorney, Agent, or Firm* — John E. Wurst; Doina G. Ene; Allergan, Inc.

(57) ABSTRACT

A composition comprising from 0.005% to 0.02% bimatoprost by weight and from 100 ppm to 250 ppm benzalkonium chloride, wherein said composition is an aqueous liquid which is formulated for ophthalmic administration is disclosed herein.

30 Claims, 2 Drawing Sheets

OTHER PUBLICATIONS

Remington, The Science and Practice of Pharmacy, 20th ed. at 831 (2000).

Remington, The Science and Practice of Pharmacy, 21st ed. at 864 (2005).

Stewart, William et al., "Corneal Punctate Staining with Latanoprost, Bimatoprost, and Travoprost in Healthy Subjects", J. Glaucoma, vol. 12, No. 6, 475-479, Dec. 2003.

XALATAN® monograph in the 59th PDR (2005).

Alm, Albert et al., "Uveoscleral Outflow—A Review", Exp. Eye Res., vol. 88(4), pp. 760-768 (Apr. 2009).

Answer, Defenses and Counterclaims of Defendants Apotex Inc. and Apotex Corp., Civil Action No. 10-CV-681, *Allergan, Inc. and Duke University v. Apotex Inc. and Apotex Corp.*, 20 pages (Nov. 22, 2010).

Bean, Gerald et al., "Commercially Available Prostaglandin Analogs for the Reduction of Intraocular Pressure: Similarities and Differences", Survey of Ophthalmology, vol. 53, Suppl. 1, pp. S69-S84 (Nov. 2008).

Berglund, Barbara et al., Investigation of Structural Analogs of Prostaglandin Amides for Binding to and Activation of $CB_1$ and $CB_2$ Cannabinoid Receptors in Rat Brain and Human Tonsils, Adv. Exp. Med. Bio., vol. 469, pp. 527-533 (1999).

Bito, Laszlo et al., The Ocular Pharmacokinetics of Eicosanoids and Their Derivatives. 1. Comparison of Ocular Eicosanoid Penetration and Distribution Following the Topical Application of $PGF_{2\alpha}$, $PGF_{2\alpha}$-1-methyl Ester, and $PGF_{2\alpha}$-1-Isopropyl Ester, Exp. Eye Res., vol. 44, pp. 217-226 (1987).

Bito, Laszlo, "Prostaglandins, Other Eicosanoids, and Their Derivatives as Potential Antiglaucoma Agents", Glaucoma: Applied Pharmacology in Medical Treatment, pp. 477-505 (1984).

Boyd, James, "Quantitative Comparison of Methods of Administering Physostigmine", Archives Ophthalmology, vol. 30(4), pp. 521-525 (1943).

Burstein, Neal, "Preservative Alteration of Corneal Permeability in Humans and Rabbits", Investigative Ophthalmology & Visual Science, vol. 25, No. 12, pp. 1453-1457 (Dec. 1984).

Cadet, Patrick et al., "Molecular identification and Functional Expression of μ 3, a Novel Alternatively Spliced Variant of the Human μ Opiate Receptor Gene", J. Immunol., vol. 170(10), pp. 5118-5123 (May 15, 2005).

Camber, Ola et al., "Influence of Some Preservatives on the Corneal Permeability of Pilocarpine and Dexamethasone, in Vitro", International Journal of Pharmaceutics, vol. 39, pp. 229-234 (1987).

Camras, Carl et al., "Detection of the Free Acid of Bimatoprost in Aqueous Humor Samples From Human Eyes Treated with Bimatoprost Before Cataract Surgery", Ophthalmology, vol. 111, No. 12, pp. 2193-2198 (2004).

Camras, Carl et al., "Bimatoprost, the Prodrug of a Prostaglandin Analogue", Br. J. Ophthalmol., vol. 92(6), pp. 862-863 (Jun. 2008).

Cantor, Louis et al., "Levels of Bimatoprost Acid in the Aqueous Humor After Bimatoprost Treatment of Patients With Cataract", Br. J. Ophthalmol., vol. 91, No. 5, pp. 629-632 (2007).

Cantor, Louis, "Reply—Bimatoprost, the Prodrug of a Prostaglandin Analogue", Br. J. Ophthalmol., vol. 92, pp. 863-864 (2008).

Collin, Barry, "Ultrastructural Changes to Corneal Stromal Cells Due to Ophthalmic Preservatives", ACTA Opthalmalogica, vol. 64, pp. 72-78 (1986).

Complaint for Patent Infringment: Civil Action No. 1:10-CV-681; *Allergan, Inc. And Duke University V. Apotex Inc. And Apotex Corp.*, 12 pages, Filed Sep. 8, 2010.

Crowston, Jonathan et al., "Effect of Bimatoprost on Intraocular Pressure in Prostaglandin FP Receptor Knockout Mice", Investigative Ophthalmology & Visual Science, vol. 46, pp. 4571-4577 (2005).

Curri, Joanne (Hi-Tech Pharmacal Co., Inc., Amityville, NY). Paragraph IV Letter to: Allergan, Inc. (Irvine, CA). 12 pages, Dec. 23, 2011.

Davies, Sean et al., "Hydrolysis of Bimatoprost (Lumigan) to its Free Acid by Ocular Tissue in Vitro", J. Ocul. Pharniacol. Ther., vol. 19(1), pp. 45-54 (Feb. 2003).

Declaration of Larry Wheeler, Ph.D., 30 pages, Dec. 14, 2010.

Faulkner, Robert et al., "Aqueous Humor Concentrations of Bimatoprost Free Acid, Bimatoprost and Travoprost Free Acid in Cataract Surgical Patients Administered Multiple Topical Ocular Doses of LUMIGAN® or TRAVATAN®", Journal of Ocular Pharmacology and Therapeutics, vol. 26, No. 2, pp. 147-156 (2010).

FDA Label for Approved NDA 22-184 of Lumigan 0.01% and Lumigan 0.03%, Aug. 31, 2010.

Frenkel, Ronald et al., "Evaluation of Circadian Control of Intraocular Pressure After a Single Drop of Bimatoprost 0.03% or Travoprost 0.004%", Curr. Med Res. Opin., vol. 24(4), pp. 919-923 (2008).

Hellberg, Mark et al., "The Hydrolysis of the Prostaglandin Analog Prodrug Bimatoprost to 17-Phenyl-trinor $PGF_{2\alpha}$ by Human and Rabbit Ocular Tissue", J. Ocular Pharmacol. Ther., vol. 19, No. 2, pp. 97-103 (2003).

Higaki, Kazutaka et al., "Estimation and Enhancement of in Vitro Corneal Transport of S-1033, a Novel Antiglaucoma Medication", International Journal of Pharmaceutics 132, pp. 165-173 (1996).

Ho, Norman et al., "Physical Model Approach to the Design of Drugs with Improved Intestinal Absorption", in Design of Biopharmaceutical Properties Through Prodrugs & Analogs, pp. 136-227 (Edward B. Roche ed., 1977).

Huang, Andrew et al., "Paracellular Permeability of Corneal and Conjunctival Epithelia", Investigative Opthalmology & Visual Sci., vol. 30, No. 4, pp. 684-289 (1989).

Jordan, Bryen et al., "G-Protein-Coupled Receptor Heterodimerization Modulates Receptor Function", Nature, vol. 399(6737), pp. 697-700 (Jun. 17, 1999).

Katz, L. Jay et al., "Comparison of Human Ocular Distribution of Bimatoprost and Latanoprost", Jul. 9, 2010 (manuscript submitted).

Kaur, Indu Pal et al., "Penetration Enhancer and Ocular Bioadhesives: Two New Avenues for Ophthalmic Drug Delivery", Drug Development and Industrial Pharmacy, vol. 28(4), pp. 353-369 (2002).

Keller, N. et al., "Increased Corneal Permeability Induced by the Dual Effects of Transient Tear Film Acidification and Exposure to Benzalkonium Chloride", Exp. Eye Res., vol. 30, pp. 203-210 (1980).

Lee, Vincent et al., "Improved Ocular Drug Delivery with Prodrugs", in Prodrugs, Topical & Ocular Drug Delivery, pp. 221-297 (1992).

Lee, Vincent et al., "Review: Topical Ocular Drug Delivery: Recent Developments and Future Challenges", Journal of Ocular Pharmacology, vol. 2, No. 1, pp. 67-108 (1986).

Liang, Y. et al., "Identification and Pharmacological Characterization of the Prostaglandin FP Receptor and FP Receptor Variant Complexes", Br. J. Pharmacol., vol. 154, pp. 1079-1093 (2008).

Lumigan®, 6 Pages, Jul. 2003.

Lumigan® 0,1 mg/ml, 3 pages, Jan. 2010.

Lyle, Donald, "Early Ocular Manifestations in the Laurence-Moon-Biedl Syndrome", Society Proceedings, J. Ophthalmology, vol. 29, pp. 939-946 (1946).

Maxey, Kirk et al., "The Hydrolysis of Bimatoprost in Corneal Tissue Generates a Potent Prostanoid FP Receptor Agonist", Surv. Ophthalmol., vol. 47, Suppl. 1, pp. S34-S40 (Aug. 2002).

Miller, William et al., "Biological Activities of 17-Pheny1-18, 19,20-Trinorprostaglandins", Prostaglandins, vol. 9, No. 1, pp. 9-18 (Jan. 1975).

Noecker, Robert et al., "Corneal and Conjunctival Changes Caused by Commonly Used Glaucoma Medications", Cornea, vol. 23, No. 5, pp. 490-496 (Jul. 2004).

Okabe, Komei et al., "Effect of Benzalkonium Chloride on Transscleral Drug Delivery", Investigative Ophthalmology & Visual Sci., vol. 46, pp. 703-708 (2005).

Pfeiffer, N. et al., "New Development in Glaucoma Drug Therapy", Ophthalmology, vol. 89, pp. W1-W13 (1992).

Poyer, John et al., "Prostaglandin $F_{2\alpha}$ Effects on Isolated Rhesus Monkey Ciliary Muscle", Invest. Ophthalmol. Vis. Sci., vol. 36(12), pp. 2461-2465 (Nov. 1995).

Remington's Pharmaceutical Sciences 1501 (15th ed. 1975).

Response from the Food and Drug Administration to Pfizer's Citizen Petition and a Supplement at 23 (Exhibit 5), 27 pages (Aug. 31, 2010).

Resul, Bahram et al., "Phenyl-Substituted Prostaglandins: Potent and Selective Antiglaucoma Agents", J. Med. Chem., vol. 36(2), pp. 243-248 (Jan. 22, 1993).

Romano, Maria et al., "Evidence for the Involvement of Cannabinoid CB₁ Receptors in the Bimatoprost-Induced Contractions on the Human Isolated Ciliary Muscle", Invest. Ophthalmol. Vis. Sci., vol. 48(8), pp. 3677-3682 (Aug. 2007).
Sandoz Paragraph 4 Letter, 19 pages, dated Jul. 11, 2011.
Schumer, Robert et al., "Medical Treatment of Glaucoma", Ophthalmology, vol. 2, pp. 140-150 (1991).
Sharif, N. A. et al., "Ocular Hypotensive FP Prostaglandin (PG) Analogs: PG Receptor Subtype Binding Affinities and Selectivities, and Agonist Potencies at FP and Other PG Receptors in Cultured Cells", J. Ocul. Pharmacol. Ther., vol. 19(6), vol. 501-15 (Dec. 2003).
Sharif, Najam et al., "Update and Commentary on the Pro-Drug Bimatoprost and a Putative Prostamide Receptor", Expert Rev. Ophthal., vol. 4(5), pp. 477-489 (2009).
Sharif, Najam et al., "Human Trabecular Meshwork Cell Responses Induced by Bimatoprost. Travoprost, Unoprostone, and Other FP Prostaglandin Receptor Agonist Analogues", Invest. Ophthalmol. Vis. Sci., vol. 44, pp. 715-721 (2003).
Sharif, Najam et al., Human Ciliary Muscle Cell Responses to FP Class Prostaglandin Analogs: Phosphoinositide Hydrolysis, Intracellular $Ca^{2+}$ Mobilization and MAP Kinase Activation, J. Ocul. Pharmacol. Ther., vol. 19, pp. 437-455 (2003).
Sharif, Najam et al., "Cat Iris Sphincter Smooth-Muscle Contraction: Comparison of FP-Class Prostaglandin Analog Agonist Activities", J. Ocul. Pharmacol. Ther., vol. 24(2), pp. 152-163 (Apr. 2008).
Sjoquist, Birgitta et al., "Pharmacokinetics of Latanoprost in the Cynomolgus Monkey. 3$^{rd}$ Communication: Tissue Distribution After Topical Administration on the Eye Studied by Whole Body Autoradiography", Glaucoma Research Laboratories, Arzneim-Forsch/Drug Res., vol. 49, pp. 240-249 (1999).
Sjoquist, Birgitta et al., "Ocular and Systemic Pharmacokinetics of Latanoprost in Humans", Surv. Ophthalmol., vol. 47 (Supp. 1), pp. S6-S12 (2002).
Spada, Clayton et al., "Bimatoprost and Prostaglandin $F_{2\alpha}$ Selectively Stimulate Intracellular Calcium Signaling in Different Cat Iris Sphincter Cells", Exp. Eye. Res., vol. 80(1), pp. 135-145 (Jan. 2005).
Stamer, W. Daniel et al., "Cellular Basis for Bimatoprost Effects on Human Conventional Outflow", Invest. Ophthalmol. Vis. Sci., vol. 51(10), pp. 5176-5181 (Oct. 2010).
Stjernschantz, Johan, "Studies on Ocular Inflammation and Development of a Prostaglandin Analogue for Glaucoma Treatment", Exp. Eye Res., vol. 78(4), pp. 759-766 (Apr. 2004).
Stjernschantz, Johan, "From $PGF_{2\alpha}$-Isopropyl Ester to Latanoprost: A Review of the Development of Xalatan: the Proctor Lecture", Invest. Ophthalmol. Vis. Sci., vol. 42(6), pp. 1134-1145 (May 2001).
Van Alphen, G.W.H.M. et al., "The Effect of Prostaglandins on the Isolated Internal Muscles of the Mammalian Eye, Including Man", Documenta Ophthalmologica, vol. 42, No. 2, pp. 397-415 (1977).
Vielhauer, George et al., "Cloning and Localization of $hFP_s$: a Six-Transmembrane mRNA Splice Variant of the Human FP Prostanoid Receptor", Arch. Biochem. Biophys., vol. 421(2), pp. 175-185 (Jan. 15, 2004).
White, Julia et al., "Heterodimerization is Required for the Formation of a Functional $GABA_B$ Receptor", Nature, vol. 396(6712), pp. 679-682 (Dec. 17, 1998).
Wilson, Stephen et al., "Dimerization of the Human Receptors for Prostacyclin and Thromboxane Facilitates Thromboxane Receptor-Mediated cAMP Generation", J. Biol. Chem., vol. 279(51 ), pp. 53036-53047 (Dec. 17, 2004).
Woodford, Roger et al., "Penetration Enhancers and the Percutaneous Absorption of Drugs : An Update", J. Toxicology-Cut. & Ocular Toxicology, vol. 5(3), pp. 167-177 (1986).
Woodward, David et al., "Bimatoprost Effects on Aqueous Humor Dynamics in Monkeys", J. Ophthalmol., 5 pages (2010).
Woodward, David et al., The Pharmacology of Bimatoprost (Lumigan™), Surv. Ophthalmol., vol. 45(Suppl 4), pp. S337-S345 (May 2001).
Woodward, David et al., "Bimatoprost: A Novel Antiglaucoma Agent", Cardiovasc. Drug Rev., vol. 22(2), pp. 103-120 (2004).
Woodward, David et al., "Pharmacological Characterization of a Novel Anti-Glaucoma agent", J. Pharmacol. Exp. Ther., vol. 305, pp. 772-785 (2003).

Woodward, David et al., "Identification of an Antagonist That Selectively Blocks the Activity of Prostamides (Prostaglandin Ethanolamides) in the Feline Iris." Br. J. Pharmacol, vol. 150, pp. 342-352 (2007).
Xalatan® Eye Drops, 3 pages, Retrieval Date : Oct. 2, 2010, http://home.intekom.com/pharm/pharmaca/xalatan.html.
Yamaji, Kazutsuna et al., "Prostaglandins $E_1$ and $E_2$, but not $F_{2\alpha}$ or Latanoprost, Inhibit Monkey Ciliary Muscle Contraction", Curr. Eye Res., vol. 30(8), pp. 661-665 (2005).
Asbjorn Tonjum, Jan. 22, 1975, Permeability of Rabbit Corneal Epithelium to Horseradish Peroxidase After the Influence of Benzalkonium Chloride, Acta Ophthalmologica, 53, 335-347.
Bito, 1985, Biological Protection with Prostanoids, CRC Press, Inc., 1, 231-252, Cohen, M. M., ed., Boca Raton, Fla., CRC Press Inc.
Bito, 1987, Prostaglandins, Old Concepts and New Perspectives, Archives of Opthalmology, 105, 1036-1039.
C.A. Lawrence, 1955, An Evaluation of Chemical Preservatives for Ophthalmic Solutions, J Am Pharm Assoc, 44 (8), 457.
C.A. Lawrence, 1955, Chemical Preservatives for Ophthalmic Solutions, Am J Ophthal, 39, 385.
C.B. Camras, Dec. 1977, Reduction of Intraocular Pressure by Prostaglandins Applied topically to the Eyes of Conscious Rabbits, Investigative Ophthalmology & Visual Science, 16(12), 1125-1134.
C.B. Camras, 1981, Reduction of Intraocular Pressure in Normal and Glaucomatous Primate (Aotus Trivirgatus) Eyes by Topically Applied Prostaglandin F2a, Current Eye Research, 1 (4), 205-209.
C.S. O'Brien, 1941, Doryl in the Treatment of Glaucoma Simplex, Tran Am Ophthal Soc, 39, 175.
C.S. O'Brien, 1942, Carbaminoyl-choline Chloride in the Treatment of Glaucoma Simplex, Arch Ophthal, 27, 253.
Center for Drug Evaluation and Research, Summary Review of Application No. 22-184 (Lumigan 0.01%) (Jul. 2010).
David Maurice, 1995, The Effect of the Low Blink Rate in Rabbits on Topical Drug Penetration, J Ocular Pharmacology and Therapeutics, 11(3), 297-304.
Diane Tang-Liu, 1994, Effects of Four Penetration Enhancers on Corneal Permeability of Drugs in Vitro, Journal of Pharmaceutical Sciences, 83 (1), 85-90.
Dwight Deardorff, 1975, Ophthalmic Preparation, Remington's Pharmaceutical Sciences, 15th ed., 1488.
F.A. Stern, 1982, Comparison of the Hypotensive and Other Ocular Effects of Prostaglandins E2 and F2a on Cat and Rhesus Monkey Eyes, Invest Ophthal Visual Sci, 22, 588-598.
F.N. Martin, 1950, Preparation of Ophthalmic Solutions With Special Reference to Hydrogen Ion Concentration and Tonicity, Arch Ophthal, 44, 561.
George Grass, Jan. 1988, Mechanisms of Corneal Drug Penetration I: In Vivo and In Vitro Kinetics, Journal of Pharmaceutical Sciences, 77 (1), 3-14.
Giuseppe Giuffre, 1985, The Effects of Prostaglandin F2a in the Human Eye, Graefe's Archive Clin. & Exper. Ophthal., 222, 139-141.
H.C. Arndt, 1977, The Synthesis and Biological Activity of Prostaglandin Analogs Containing Spirocyclic Rings, Prostaglandins, 13 (5), 837-843.
Handbook of Pharmaceutical Excipients, Monographs for Water, Sodium Phosphate, Sodium Chloride, and Citric Acid Monohydrate (1994).
Harvey Dubiner, 2001, Efficacy and Safety of Bimatoprost in Patients With Elevated Intraocular Pressure: a 30-Day Comparison With Latanoprost, Surv. Ophthalmol, 45 (4), S353-S560.
Hitoshi Sasaki, 1995, Ocular Permeability of FITC-Dextran with Absorption Promoter for Ocular Delivery of Peptide Drug, J Drug Target, 3, 129.
Hitoshi Sasaki, 1995, Ophthalmic Preservatives As Absorption Promoters for Ocular Drug Delivery, J. Pharm. Pharmacol., 47, 703-707.
Hitoshi Sasaki, 2000, Modification of Ocular Permeability of Peptide Drugs by Absorption Promoters, Biol Pharm Bull, 23(12), 1524.
J. Thygesen, 2000, Short-term Effect of Latanoprost and Timolol Eye Drops on Tear Fluid and the Ocular Surface in Patients with Primary Open-Angle Glaucoma and Ocular Hypertension, Acta Ophthal Scand, 78, 37-41.

Jay Katz, 2010, Twelve-Month, Randomized, Controlled Trial of Bimatoprost 0.01%, 0.0125%, and 0.03% in Patients with Glaucoma or Ocular Hypertension, Am J Ophthalmology, 149(4), 661-671.

Ke-Ping Xu, 2000, Corneal Organ Culture Model for Assessing Epithelial Responses to Surfactants, Tox. Sci., 58, 306.

Keith Green, 1971, Influence of Various Agents on Corneal Permeability, American Journal of Ophthalmology, 72, 897-905.

Martina Scholz, 2002, Pilocarpine Permeability Across Ocular Tissues and Cell Cultures: Influence of Formulation Parameters, Journal of Ocular Pharmacology and Therapeutics, 18 (5), 455-468.

Michael Brown, 1967, Control of Contamination in Ophthalmic Solutions, Proc. R. Sco. Med., 60, 354-357.

Milton Skolaut, 1948, Ophthalmic Medication, Bull Am Soc Hosp Pharm, 5(4), 172.

Modell Walter, 1947, Pharmacologic Action of Some Ophthalmic Drugs, Arch Ophthal, 37, 160.

Neal Burstein, 1980, Preservative Cytotoxic Threshold for Benzalkonium Chloride and Chlorhexidine Digluconate in Cat and Rabbit Corneas, Invest. Ophthal. & Visual Sci., 19 (3), 308-313.

Nilsson, 1987, PGF 2a Increases Uveoscleral Outflow, Invest. Ophthalmol. Vis. Sci, 28 (Suppl), 284.

P. De Clercq, 1976, Cyclopentanones-VXL., Prostaglandin Synthesis Involving Catalytic Hydrogenation of 2,3-Dialkyl-4-Hydroxy-2-Cyclopentenones, Tetrahedron, 32, 2747-2752.

Paul Ashton, 1991, Formulation Influence on Conjunctival Penetration of Four Beta Blockers in the Pigmented Rabbit: A Comparison with Corneal Penetration, Pharmaceutical Research, 8 (9), 1166-1174.

Physicians' Desk Reference, 56th ed., pp. 212-213, 543, 553-554, 2864-65 (2002).

Physicians' Desk Reference, 59th ed., pp. 555-556 (2005).

Pierre-Jean Pisella, 2004, Conjunctival Proinflammatory and Proapoptotic Effects of Latanoprost and Preserved and Unpreserved Timolol: An Ex Vivo and In Vitro Study, Investigative Ophthalmology & Visual Science, 45, 1360-1368.

Pieter Van Der Bijl, 2001, Effects of Three Penetration Enhancers on Transcorneal Permeation of Cyclosporine, Cornea, 20 (5), 505-508.

R. Roggeband 2000, Eye Irritation in Rabbit and Man After Single Applications of Equal Volumes of Undiluted Model Liquid Detergent Products, Food & Chem Toxic, 38, 727.

Richard Parrish, 2003, A Comparison of Latanoprost, Bimatoprost, and Travoprost in Patients With Elevated Intraocular Pressure: A 12-Week, Randomized, Masked Evaluator Multicenter Study, Am J Ophthalmol, 135, 688-703.

Robert Laibovitz, 2001, Comparison of the Ocular Hypotensive Lipid AGN 192024 With Timolol, Arch Ophthal, 119, 994.

Robert Noecker, 2003, Bimatoprost/Latanoprost Study Group. A Six Month Randomized Clinical Trial Comparing the Intraocular Pressure Lowering Efficacy of Bimatoprost and Latanoprost in Patients With Ocular Hypertension or Glaucoma, Am J Ophthal, 135, 55-63.

Samir Podder, 1992, Improving the Safety of Topically Applied Timolol in the Pigmented Rabbit Through Manipulation of Formulation Composition, Exp. Eye Res., 54, 747-757.

Samuel McPherson, 1949, Self-Sterilizing Ophthalmic Solutions, Am J Ophthal, 32, 675.

Starr, 1971, Further Studies on the Effects of Prostagladin on Intraocular Pressure in the Rabbit, Exp. Eye Res., 11, 170-177.

Stefano Gandolfi, 2001, Three-month Comparison of Bimatoprost and Latanoprost in Patients With Glaucoma and Ocular Hypertension, Adv. Ther., 18, 110-121.

Thomas Honohan, 1980, Duration of Activity of the Acid, Methyl Ester and Amide of an Orally Active Platelet Aggregation Inhibitory Prostanoid in the Rat, Prostoglandins, 19, 139.

Thomas Walter, 2004, 24-Hour IOP Control with Once-daily Bimatoprost, Timolol Gel-forming Solution, or Latanoprost: A 1-Month, Randomized, Comparative Clinical Trial, Survey of Ophthalmology, 49(1), S26-S35.

William Mullen, 1973, Ophthalmic Preservatives and Vehicles, Sury Ophthal, 17(6), 469.

ENHANCED BIMATOPROST OPHTHALMIC SOLUTION

CROSS-REFERENCE TO RELATED APPLICATION

This application is a continuation of U.S. patent application Ser. No. 12/965,514, filed Dec. 10, 2010 which is a continuation of U.S. patent application Ser. No. 11/083,261, filed Mar. 16, 2005, which is incorporated herein by reference in its entirety.

FIELD OF THE INVENTION

This invention relates to pharmaceutical compositions comprising bimatoprost.

BACKGROUND OF THE INVENTION

Description of Related Art

Bimatoprost, shown below, is a prostamide marketed commercially for the treatment of glaucoma and ocular hypertension.

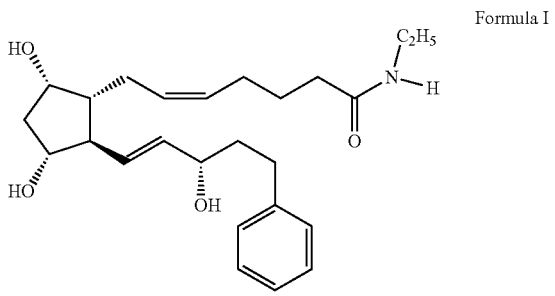

Formula I

Benzalkonium chloride (BAK) is a preservative used in many commercial ophthalmic products to prevent microbial contamination in multi-use products. The commercial eye drops (Bimatoprost, Allergan, Inc., Irvine, Calif.) contain 0.03% bimatoprost and 0.005% BAK. Although no other prostamides are currently marketed for the treatment of glaucoma, several prostaglandin analogs are commercially available which use BAK as a preservative. These include latanoprost (Xalatan), travoprost (Travatan), and unoprostone isopropyl (Rescula), which require significantly more BAK, from 150-200 ppm, to meet antimicrobial effectiveness tests in the United States and Europe.

U.S. Pat. No. 6,596,765 B2 discloses a composition comprising 0.005% or 0.0005% latanoprost and 0.2 mg/mL BAK.

U.S. Pat. No. 6,646,001 B2 discloses compositions comprising 0.03% bimatoprost and 0.01% BAK or "0.01%+5% excess" BAK.

BRIEF DESCRIPTION OF THE DRAWING FIGURES

DETAILED DESCRIPTION OF THE INVENTION

Figure 1:
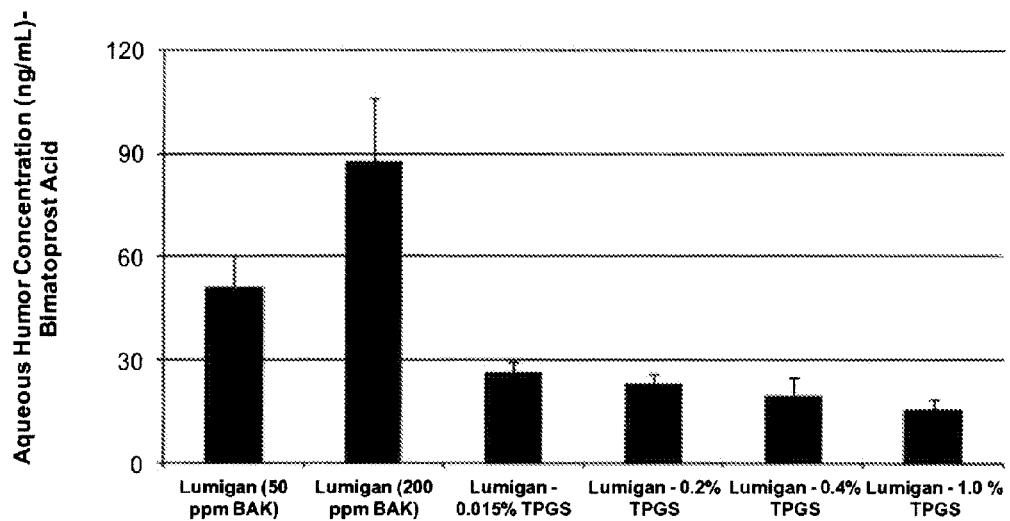
FIG. 1 is a plot showing the aqueous humor concentration of the parent acid of bimatoprost after topical administration of several formulations.

A composition comprising from 0.005% to 0.02% bimatoprost by weight and from 100 ppm to 250 ppm benzalkonium chloride, wherein said composition is an aqueous liquid which is formulated for ophthalmic administration is disclosed herein.

A method which is useful in treating glaucoma or ocular hypertension related thereto is also disclosed herein.

An aqueous liquid which is formulated for ophthalmic administration is formulated such that it can be administered topically to the eye. The comfort should be maximized as much as possible, although sometimes formulation considerations (e.g. drug stability) may necessitate less than optimal comfort.

In certain compositions the concentration of bimatoprost is from 0.01% to 0.02%. In other compositions the concentration of bimatoprost is from 0.015% to 0.02%.

In certain compositions the concentration of BAK is from 150 ppm to 200 ppm. In other compositions the concentration of BAK is from 150 ppm to 200 ppm. In other compositions the concentration of BAK is from 150 ppm to 250 ppm.

In ophthalmic compositions, a chelating agent may be used to enhance preservative effectiveness. Suitable chelating agents are those known in the art, and, while not intending to be limiting, edetate salts (EDTA) are useful chelating agents.

In certain compositions, concentration of EDTA is at least 0.001%. In other compositions, the concentration of EDTA is at least 0.01%. In other compositions the concentration of EDTA is 0.15% or less. In other compositions the concentration of EDTA is 0.1% or less. In other compositions the concentration of EDTA is 0.05% or less.

Certain compositions comprise from 150 to 250 ppm BAK and an effective amount of EDTA.

As is known in the art, buffers are commonly used to adjust the pH to a desirable range for ophthalmic use. Generally, a pH of around 6-8 is desired, and in certain compositions a pH of 7.4 is desired. Many buffers including salts of inorganic acids such as phosphate, borate, and sulfate are known.

Another commonly used excipient in ophthalmic compositions is a viscosity-enhancing, or a thickening agent. Thickening agents are used for a variety of reasons, ranging from improving the form of the formulation for convenient administration to improving the contact with the eye to improve bioavailability. The viscosity-enhancing agent may comprise a polymer containing hydrophilic groups such as monosaccharides, polysaccharides, ethylene oxide groups, hydroxyl groups, carboxylic acids or other charged functional groups. While not intending to limit the scope of the invention, some examples of useful viscosity-enhancing agents are sodium carboxymethylcellulose, hydroxypropylmethylcellulose, povidone, polyvinyl alcohol, and polyethylene glycol.

In ophthalmic solutions, tonicity agents often are used to adjust the composition of the formulation to the desired isotonic range. Tonicity agents are well known in the art and some examples include glycerin, mannitol, sorbitol, sodium chloride, and other electrolytes.

One composition has a pH of 7.4 and consists essentially of 0.015% bimatoprost, 200 ppm benzalkonium chloride, from 0 to 0.03% EDTA, a phosphate buffer, NaCl, and water.

Another composition has a pH of 7.4 and comprises 0.02% bimatoprost, 200 ppm benzalkonium chloride, from 0 to 0.03% EDTA, a phosphate buffer, NaCl, and water.

Another composition has a pH of 7.4 and consists of 0.01% bimatoprost, 200 ppm benzalkonium chloride, from 0 to 0.03% EDTA, a phosphate buffer, NaCl, and water.

The best mode of making and using the present invention are described in the following examples. These examples are given only to provide direction and guidance in how to make and use the invention, and are not intended to limit the scope of the invention in any way.

One embodiment comprises 0.01% Bimatoprost, 0.02% Benzalkonium Chloride, 0.268% Sodium Phosphate Dibasic, Heptahydrate, 0.014% Citric Acid, Monohydrate, 0.81% Sodium Chloride, and water, wherein the pH is 7.3.

Another embodiment comprises 0.015% Bimatoprost, 0.02% Benzalkonium Chloride, 0.268% Sodium Phosphate Dibasic, Heptahydrate, 0.014% Citric Acid, Monohydrate, 0.81% Sodium Chloride, and water, wherein the pH is 7.3.

Another embodiment comprises 0.015% Bimatoprost, 0.02% Benzalkonium Chloride, 0.268% Sodium Phosphate Dibasic, Heptahydrate, 0.014% Citric Acid, Monohydrate, 0.81% Sodium Chloride, 0.03%, EDTA, and water, wherein the pH is 7.3.

Another embodiment comprises 0.02% Bimatoprost, 0.02% Benzalkonium Chloride, 0.268% Sodium Phosphate Dibasic, Heptahydrate, 0.014% Citric Acid, Monohydrate, 0.81% Sodium Chloride, and water, wherein the pH is 7.3.

Another embodiment consists essentially of 0.01% Bimatoprost, 0.02% Benzalkonium Chloride, 0.268% Sodium Phosphate Dibasic, Heptahydrate, 0.014% Citric Acid, Monohydrate, 0.81% Sodium Chloride, and water, wherein the pH is 7.3.

Another embodiment consists essentially of 0.015% Bimatoprost, 0.02% Benzalkonium Chloride, 0.268% Sodium Phosphate Dibasic, Heptahydrate, 0.014% Citric Acid, Monohydrate, 0.81% Sodium Chloride, and water, wherein the pH is 7.3.

Another embodiment consists essentially of 0.015% Bimatoprost, 0.02% Benzalkonium Chloride, 0.268% Sodium Phosphate Dibasic, Heptahydrate, 0.014% Citric Acid, Monohydrate, 0.81% Sodium Chloride, 0.03%, EDTA, and water, wherein the pH is 7.3.

Another embodiment consists essentially of 0.02% Bimatoprost, 0.02% Benzalkonium Chloride, 0.268% Sodium Phosphate Dibasic, Heptahydrate, 0.014% Citric Acid, Monohydrate, 0.81% Sodium Chloride, and water, wherein the pH is 7.3.

Another embodiment consists of 0.01% Bimatoprost, 0.02% Benzalkonium Chloride, 0.268% Sodium Phosphate Dibasic, Heptahydrate, 0.014% Citric Acid, Monohydrate, 0.81% Sodium Chloride, and water, wherein the pH is 7.3.

Another embodiment consists of 0.015% Bimatoprost, 0.02% Benzalkonium Chloride, 0.268% Sodium Phosphate Dibasic, Heptahydrate, 0.014% Citric Acid, Monohydrate, 0.81% Sodium Chloride, and water, wherein the pH is 7.3.

Another embodiment consists of 0.015% Bimatoprost, 0.02% Benzalkonium Chloride, 0.268% Sodium Phosphate Dibasic, Heptahydrate, 0.014% Citric Acid, Monohydrate, 0.81% Sodium Chloride, 0.03%, EDTA, and water, wherein the pH is 7.3.

Another embodiment consists of 0.02% Bimatoprost, 0.02% Benzalkonium Chloride, 0.268% Sodium Phosphate Dibasic, Heptahydrate, 0.014% Citric Acid, Monohydrate, 0.81% Sodium Chloride, and water, wherein the pH is 7.3.

EXAMPLE 1

Formulations containing 0.268% sodium phosphate dibasic heptahydrate, 0.014% citric acid, 0.83% sodium chloride, with the pH adjusted to 7.3 in qs water, and the amounts of bimatoprost, BAK, and EDTA listed in Table 1 below were prepared by conventional methods well known in the art.

TABLE 1

| Formulation |
| --- |
| 1. 0.03% Bimatoprost (50 ppm BAK) Control |
| 2. 0.03% Bimatoprost - 200 ppm BAK |
| 3. 0.03% Bimatoprost - 0.015% TPGS (no preservative) |
| 4. 0.03% Bimatoprost - 0.2% TPGS (no preservative) |
| 5. 0.03% Bimatoprost - 0.4% TPGS (no preservative) |
| 6. 0.03% Bimatoprost - 1.0% TPGS (no preservative) |

EXAMPLE 2

Studies were carried out to determine the effect of benzalkonium chloride (BAK) and d-alpha tocopheryl polyethylene glycol 1000 succinate (TPGS) on ocular absorption of bimatoprost in vivo. For the in vivo study, eighteen female rabbits were given a single 28 μL eyedrop bilaterally and aqueous humor samples were collected (n=3 animals with 6 eyes per formulation) at 60 min postdose. Two rabbits (4 eyes) remained untreated to serve as pre-dose bioanalytical controls. Bimatoprost and its parent carboxylic acid extracted from aqueous humor and in vitro samples were analyzed by a liquid chromatography tandem mass spectrometry (LC-MS/MS) method with a quantitation range of 0.25-60 ng/mL.

Due to extensive metabolism of bimatoprost in rabbit eyes, its parent acid was used as a surrogate for determining ocular absorption of bimatoprost. Concentration of the acid in rabbit aqueous humor following single dose of 6 different bimatoprost formulations are summarized in FIG. 1 and Table 2 below.

TABLE 2

| Formulation | Aqueous Humor[a] (ng/mL) |
| --- | --- |
| 1. 0.03% Bimatoprost (50 ppm BAK) Control | 51.0 ± 9.4 |
| 2. 0.03% Bimatoprost - 200 ppm BAK | 87.2 ± 19.0* |
| 3. 0.03% Bimatoprost - 0.015% TPGS (no preservative) | 26.1 ± 3.3* |
| 4. 0.03% Bimatoprost - 0.2% TPGS (no preservative) | 22.9 ± 3.2* |
| 5. 0.03% Bimatoprost - 0.4% TPGS (no preservative) | 19.3 ± 5.6* |
| 6. 0.03% Bimatoprost - 1.0% TPGS (no preservative) | 15.4 ± 3.3* |

[a]Mean ± SD. Per formulation, N = 3 rabbits (6 eyes).
*Statistically different ($p < 0.05$) compared to 0.03% Bimatoprost Test formulations containing 0.015%, 0.2%, 0.4% and 1.0% TPGS resulted in a lower aqueous humor carboxylic acid concentration compared to Bimatoprost by 52%, 59%, 62% and 72%, respectively. In contrast, 0.03% Bimatoprost containing 200 ppm BAK resulted in 57% higher aqueous humor AGN 191522 concentration compared to Bimatoprost (50 ppm BAK).

While not intending to limit the scope of the invention in any way, or be bound by theory, compared to the Bimatoprost control, formulations containing TPGS resulted in decrease bimatoprost permeability. In contrast, formulations with higher BAK resulted in higher permeability.

EXAMPLE 3

Formulations containing 0.268% sodium phosphate dibasic heptahydrate, 0.014% citric acid, 0.83% sodium chloride, with the pH adjusted to 7.3 in qs water, and the amounts of bimatoprost, BAK, and EDTA listed in Table 3 below were prepared by conventional methods well known in the art.

TABLE 3

| | Formulation |
|---|---|
| A. | 0.03% Bimatoprost (50 ppm BAK) - Control |
| B. | 0.015% Bimatoprost (50 ppm BAK) |
| C. | 0.015% Bimatoprost (50 ppm BAK) 0.03% EDTA |
| D. | 0.015% Bimatoprost (200 ppm BAK) |
| E. | 0.015% Bimatoprost (200 ppm BAK) 0.03% EDTA |
| F. | 0.015% Bimatoprost (50 ppm BAK) 0.015% EDTA |
| G. | 0.015% Bimatoprost (200 ppm BAK) 0.015% EDTA |
| H. | 0.015% Bimatoprost (125 ppm BAK) |
| I. | 0.015% Bimatoprost (125 ppm BAK) 0.03% EDTA |
| J. | 0.015% Bimatoprost (125 ppm BAK) 0.015% EDTA |
| K. | 0.015% Bimatoprost (150 ppm BAK) |
| L. | 0.015% Bimatoprost (150 ppm BAK) 0.1% EDTA |
| M. | 0.015% Bimatoprost |
| N. | 0.03% Bimatoprost |

EXAMPLE 4

The effect of benzalkonium chloride (BAK) and ethylenediaminetetraacetic acid (EDTA) on bimatoprost permeability across primary culture of rabbit corneal epithelial cell layers (RCECL). Corneal epithelial cells were harvested from New Zealand White rabbits and cultured on Transwell™ filters until confluency (Day 5). For the transport experiment, cells were first equilibrated in transport buffer for 1 hour at 37° C. Dosing solution containing 0.015% or 0.03% bimatoprost with varying concentrations of BAK and EDTA was then applied to the apical compartment of the Transwell™ (2 cultures; n=3-4 per culture) and the cells were incubated at 37° C. At 30, 60, 90 and 120 minutes postdose, 200 µL samples were taken from the basolateral chamber for apical to basolateral (AB) transport. The samples were analyzed by a liquid chromatography tandem mass spectrometry (LC-MS/MS) method with quantitation range of 1-600 ng/mL.

Figure 2:
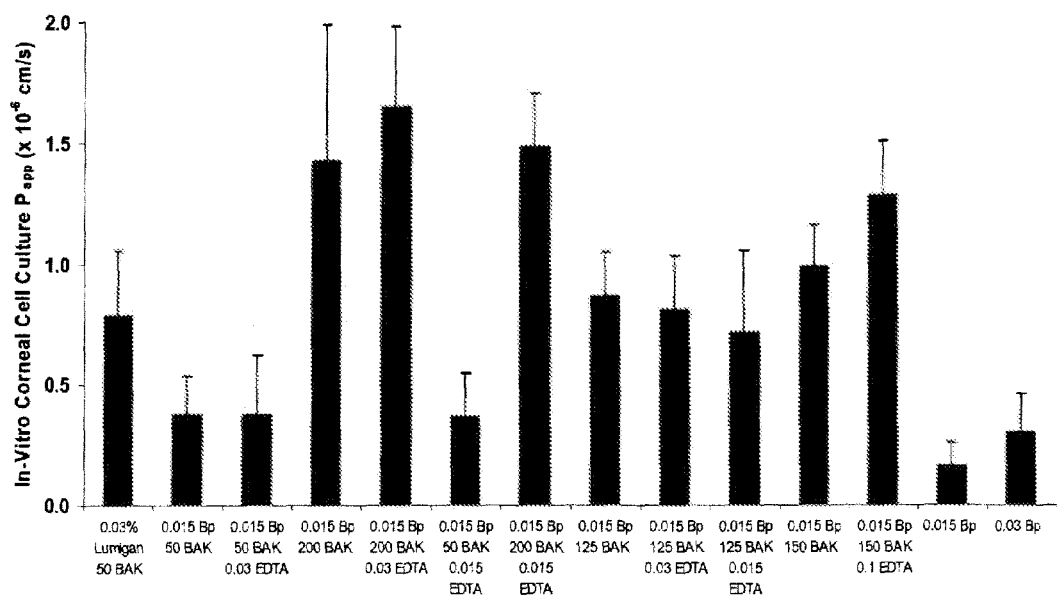
FIG. 2 is a plot showing the membrane permeability of bimatoprost in several different formulations.

The results are presented in FIG. 2.

EXAMPLE 5

A drop of formulation J is administered once daily topically to the eye of a person suffering from glaucoma. After a few hours, intraocular pressure drops more and less hyperemia is observed than would be observed for formulation A. Lowered intraocular pressure persists for as long as the treatment continues.

What is claimed is:

1. A first composition administered once daily for lowering intraocular pressure in a person with glaucoma or ocular hypertension, the first composition comprising about 0.01% w/v bimatoprost and about 0.02% w/v benzalkonium chloride, wherein the first composition lowers intraocular pressure and results in less hyperemia as compared to the once daily administration of a second composition comprising 0.03% w/v bimatoprost and 0.005% w/v benzalkonium chloride.

2. The composition of claim 1 wherein the first composition has a pH of about 7.3.

3. The composition of claim 1 wherein the first composition comprises 0.01% w/v bimatoprost and 0.02% w/v benzalkonium chloride.

4. The composition of claim 1 wherein the first composition has at least one buffering agent selected from the group consisting of dibasic sodium phosphate heptahydrate, citric acid monohydrate and EDTA.

5. The composition of claim 1 wherein the first composition is effective in treating glaucoma.

6. The composition of claim 1 wherein the first composition is effective in treating ocular hypertension.

7. A first composition administered once daily for lowering intraocular pressure in a person with glaucoma or ocular hypertension, the first composition comprising about 0.01% w/v bimatoprost and about 0.02% w/v benzalkonium chloride, wherein the first composition lowers intraocular pressure without a substantial reduction in the intraocular pressure lowering benefit provided by the once daily administration of a second composition comprising 0.03% w/v bimatoprost and 0.005% w/v benzalkonium chloride.

8. The composition of claim 7 wherein the once daily administration of the first composition results in less hyperemia as compared to the once daily administration of the second composition.

9. The composition of claim 7 wherein the first composition has a pH of about 7.3.

10. The composition of claim 7 wherein the first composition comprises 0.01% w/v bimatoprost and 0.02% w/v benzalkonium chloride.

11. The composition of claim 7 wherein the first composition has at least one buffering agent selected from the group consisting of dibasic sodium phosphate heptahydrate, citric acid monohydrate and EDTA.

12. The composition of claim 7 wherein the first composition is applied topically.

13. The composition of claim 7 wherein the first composition is effective in treating glaucoma.

14. The composition of claim 7 wherein the first composition is effective in treating ocular hypertension.

15. A first composition for reducing the amount of bimatoprost administered to a person in a once daily treatment for glaucoma or ocular hypertension, the first composition comprising about 0.01% w/v bimatoprost and about 0.02% w/v benzalkonium chloride, wherein first the composition remains useful in treating glaucoma or ocular hypertension despite a lower concentration of bimatoprost as compared to the once daily administration of a second composition comprising 0.03% w/v bimatoprost and 0.005% w/v benzalkonium chloride.

16. The composition of claim 15 wherein the once daily administration of the first composition results in less hyperemia as compared to the once daily administration of the second composition.

17. The composition of claim 15 wherein the first composition has a pH of about 7.3.

18. The composition of claim 15 wherein the first composition comprises 0.01% w/v bimatoprost and 0.02% w/v benzalkonium chloride.

19. The composition of claim 15 wherein the first composition is a solution.

20. The composition of claim 15 wherein the first composition is effective in treating glaucoma.

21. The composition of claim 20 wherein the glaucoma is open-angle glaucoma.

22. The composition of claim 15 wherein the first composition is effective in treating ocular hypertension.

23. A first composition for reducing the amount of bimatoprost administered to a person in a once daily treatment for glaucoma or ocular hypertension, wherein the first composition comprises about 0.01% w/v bimatoprost and about 0.02% w/v benzalkonium chloride, wherein the benzalkonium chloride concentration of the first composition increases the permeability of bimatoprost across corneal epithelial cell layers as compared to the once daily administration of a second composition comprising 0.03% w/v bimatoprost and 0.005% w/v benzalkonium chloride.

24. The composition of claim 23 wherein the first composition remains useful in treating glaucoma or ocular hypertension despite a lower concentration of bimatoprost as compared to the second composition.

25. The composition of claim 23 wherein the first composition results in less hyperemia as compared to the once daily administration of the second composition.

26. The composition of claim 23 wherein the first composition is effective in treating glaucoma.

27. The composition of claim 23 wherein the composition is effective in treating ocular hypertension.

28. The composition of claim 23 wherein the first composition has a pH of about 7.3.

29. The composition of claim 23 wherein the first composition has at least one buffering agent selected from the group consisting of dibasic sodium phosphate heptahydrate, citric acid monohydrate and EDTA.

30. The composition of claim 23 wherein the first composition comprises 0.01% w/v bimatoprost and 0.02% w/v benzalkonium chloride.

* * * * *